US006194146B1

United States Patent
Utermohlen et al.

(10) Patent No.: US 6,194,146 B1
(45) Date of Patent: *Feb. 27, 2001

(54) SITU AND IN VITRO HYBRIDIZATION METHOD AND BUFFER

(75) Inventors: Joseph G. Utermohlen; David W. Sammons, both of Tucson, AZ (US)

(73) Assignee: BioSeparations, Inc., Tucson, AZ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/949,243

(22) Filed: Oct. 10, 1997

Related U.S. Application Data

(63) Continuation-in-part of application No. 08/874,270, filed on Jun. 13, 1997, now Pat. No. 5,948,617.

(51) Int. Cl.$^7$ .............................. C12Q 1/68; C07H 21/02; C07H 21/04; C12N 15/00
(52) U.S. Cl. ........................... 435/6; 536/23.1; 536/24.3; 935/76; 935/77; 935/78
(58) Field of Search .............................. 435/6; 536/23.1, 536/24.3; 935/76, 77, 78

(56) References Cited

U.S. PATENT DOCUMENTS

| | | | |
|---|---|---|---|
| 4,302,204 | 11/1981 | Wahl et al. | 23/230.3 |
| 4,358,535 | 11/1982 | Falkow et al. | 435/5 |
| 4,647,529 | 3/1987 | Rodland et al. | 435/6 |
| 4,689,294 | 8/1987 | Boguslawski | 435/6 |
| 4,886,741 | 12/1989 | Schwartz | 435/5 |
| 4,888,278 | 12/1989 | Singer et al. | 435/6 |
| 5,132,207 | 7/1992 | Kohne et al. | 435/6 |
| 5,225,326 | 7/1993 | Bresser et al. | 435/6 |
| 5,232,831 | 8/1993 | Milliman et al. | 435/6 |
| 5,316,906 | 5/1994 | Haugland et al. | 435/4 |
| 5,447,841 | 9/1995 | Gray et al. | 435/6 |

(List continued on next page.)

FOREIGN PATENT DOCUMENTS

| | | |
|---|---|---|
| WO90/02204 | 8/1990 | (WO) . |
| WO95/03431 | 2/1995 | (WO) . |
| WO96/00234 | 4/1996 | (WO) . |
| WO96/31626 | 10/1996 | (WO) . |

OTHER PUBLICATIONS

Tagarro et al., Human Genetics 93 : 383–388 (1994).*
"Fluorescent in situ Hybridization for the Diagnosis of Genetic Disease at Postnatal, Prenatal, and Preimplantation Stages" by Darren K. Griffin *International Revew of Cytology* vol. 153, pp. 1–35 (1994).
"A Rapid FISH Technique for Quantitative Microscopy" by F.M. Haar, et al. *Biotechniquest Research Reports* vol. 17, No. 2, pp. 346–353 (1994).

"Rapid Detection of Chromosome Aneuploidies in Uncultered Amniocytes by Using Fluorescence In Situ Hybridization (FISH)" by Katherine Klinger, et al. *Am. J. Human Genet.* vol. 51, pp. 55–65 (1992).
"Detection of Aneuploidy Involving Chromosomes 13, 18 or 21 by Fluorescence In Situ Hybridization (FISH) to Interphase and Metaphase Amniocytes" by Wen–Lin Kuo, et al. *Am. j. Human Genet.* vol. 49, pp. 112–119 (1991).
"Rapid Prenatal Diagnosis of Chromosomal Aneuploidies by Fluorescence In Situ Hybridization: Clinical Experience with 4,500 Specimens" by Brian E. Ward, et al. *Am J. Human Genet.* vol. 52, pp. 854–865 (1993).
"Fast Hybridization Solution for the Detection of Immobilized Nucleic Acids" by Te–Tuan Yang, et al. *Biotechniques Research Reports*, vol. 18, No. 3, pp. 498–503 (1995).
"ExpressHyb Hybridization Solution" by Clontech Laboratories, Inc. *Catalog #8015 Product Protocol*, pp. 1, 5, 7, 9, and 11 (no date).
"Cy3™–Chromosome X Human Alpha–Satellite Specific Probe Cat. No. A6300X" by Biological Detection Systems, Inc. *Cyprobe Pamphlet* (No date).
"Formamide" by Fisher Scientific, Inc. *Material Safety Data Sheet*, pp. 1–4 (1995).
"Rapid Hybridization Protocol for Direct–Labeled (FITC or Texas Red) Satellite DNA Probes" by Oncor, Inc. *Oncor Detection Kit: Rapid Chromosome In Situ Hybridization System*, Edition 1, pp. 1–13 (Oct. 1993).
"Spectrum CEP Direct Chromosome Enumeration System" by Imagentics, Inc. *Imagentics Pamphlet (Prodecural Kit)* (No date).
"Nucleic Acid Hybridization: From Research Tool to Routine Diagnostic Method" by A.C. Syvänen *Medical Biology (Review Article)*, vol. 64, pp. 313–324 (1996).
"A Manual for Genetic Engineering, Advanced Bacterial Genetics" by Ronald W. Davis, et al. article from Cold Spring Harbor Laboratory (1980).
"Molecular Cloning, A Laboratory Manual" by T. Maniatis, et al. article from Cold Spring Harbor Laboratory, pp. 338–389 (1982).
"AproProbe™ Plus" by Aprogenex, Inc. *Aprogenex pamphlet* (No date).
"Renaturants and Preservatives", 1 page pamphlet (no date).
"Vysis FISH Technology and Nucleic Acid Probes" by Vysis, Inc. (Mar. 1997).
"Detection of chromosome aberrations in the human interphase nucleus by visualization of specific target DNAs with radioactive and non–radioactive in situ hybridization techniques: Diagnosis of trisomy 18 with Probe L.84", by T. Cremer, et al. *Hum Genet*, vol. 74, pp. 346–352 (1986).

(List continued on next page.)

*Primary Examiner*—Ethan Whisenant
(74) *Attorney, Agent, or Firm*—David G. Rosenbaum

(57) ABSTRACT

A method and single solution denaturation and hybridization useful with probes for hybridizing DNA or RNA sequences. The inventive protocol employs a carbinol containing hybridization solution.

4 Claims, 4 Drawing Sheets

U.S. PATENT DOCUMENTS

| | | | |
|---|---|---|---|
| 5,506,098 | 4/1996 | Zarling et al. | 435/6 |
| 5,512,436 | 4/1996 | Stone | 435/6 |
| 5,521,061 | 5/1996 | Bresser et al. | 435/517 |
| 5,750,340 * | 5/1998 | Kim et al. | 435/6 |

OTHER PUBLICATIONS

"Cytogenetic analysis using quantitative, high sensitivity, fluorescence hybridization" by D. Pinkel, T. Straume, and J.W. Gray, *Proc Nat'l Acad Sci USA*, vol. 83, pp. 2934–2938 (No date).

\* cited by examiner

SITU AND IN VITRO HYBRIDIZATION METHOD AND BUFFER

CROSS-REFERENCE TO RELATED APPLICATIONS

This application is a continuation-in-part of U.S. patent application Ser. No. 08/874,270, filed Jun. 13, 1997 now U.S. Pat. No. 5,948,617 which is commonly assigned and which is hereby incorporated by reference.

BACKGROUND OF THE INVENTION

The present invention relates generally to in situ and in vitro hybridization methods and hybridization buffers for labeling of genomic DNA and RNA. More particularly, the present invention relates to novel hybridization buffer compositions useful in conjunction with biologic and synthetic probes for hybridizing DNA or RNA sequences by fluorescence in situ hybridization ("FISH") and blot hybridization methodologies. In all aspects of the present invention, the criteria for success included: 1) ease of procedure, 2) reliability, 3) hybridization specificity, 4) hybridization efficiency, 5) brightness of the fluorescence signal, 6) stability of the labeled hybrid, and 7) conservation of the cellular and nuclear morphology.

By reference to blot hybridization technology, conventional FISH technology is dependent upon formamide chemistry for DNA denaturation, hybridization buffers, and post-hybridization washes. (Cremer T., Landegent J., Brueckner A., Scholl H P, Schardin M, Hager H D, Devilee P. Pearson P. van der Ploeg M. (1986), "Detection of chromosome aberrations in the human interphase nucleus by visualization of specific target DNAs with radioactive and non-radioactive in situ hybridization techniques: diagnosis of trisomy 18 with probe L.84," *Hum. Genet* 74:346–352; Pinkel D, Straume T. Gray J W. (1986) "Cytogenetic analysis using quantitative, high-sensitivity, fluorescence hybridization," *Proc Natl Acad Sci USA* 83 :2934–2938). The entire procedure includes multiple steps for sample denaturation, hybridization and post-hybridization washes. This process often takes hours to yield a fluorescent label with a signal intensity sufficient for routine chromosome enumeration. Although some recent improvements of formamide-based FISH have been introduced, for example the use of co-denaturation of probes and sample and the elimination of formamide in the post-hybridization washes (Abati A, Sanford J. Fetsch P. Marincola F. Wolman S. (1995) "Fluorescence in situ hybridization (FISH): a user's guide to optimal preparation of cytologic specimens," *Diagnostic Cytopathology* 13:5:486–492), the chemistry of the hybridization reaction is still based on formamide. Known disadvantages of formamide are that it reduces the kinetics of hybridization (Kourilsky Ph. Leidner J. Tremblay. 1971 "DNA—DNA hybridization on filters at low temperature in the presence of formamide or urea, *Biochimie* 53:1111–1114), oxides easily, and is a known teratogen.

Currently, most clinical laboratories use FISH kits available from the following commercial sources: Oncor, Inc. or Vysis, Inc. Both the Oncor and the Vysis probes are of biological origin their protocols require formamide containing hybridization solutions. Another current kit for conducting FISH is available from Aprogenex, Inc. and is sold under the trademark APROPROBE PLUS. The APROPROBE PLUS FISH kit utilizes synthetic oligonucleotide fluorophore-labeled probes specific for the centromeric region of human chromosomes X, Y, 13/21 and 18 and the mRNA of gamma globin. The hybridization solution provided with the APROPROBE PLUS FISH kit also contains formamide. See, also, Bresser, et al., U.S. Pat. No. 5,225,326, which teaches the use of formamide-based hybridization solution with oligonucleotide probes.

Non-formamide-based hybridization solutions for conducting FISH analysis are known in the art, as more fully disclosed in co-pending U.S. patent application Ser. No. 08/418,704, filed Apr. 7, 1995, published as International Application WO 96/31626, published on Oct. 10, 1996, which discloses use of a glycerol and dextran sulfate hybridization buffer for FISH labeling of human chromosomes using clone probes. However, when the teachings of International Application WO 96/31626, were followed using synthetic oligonucleotide DNA probes, such those available in the APROPROBE PLUS FISH Kit (Aprogenex, Inc.) or those disclosed in International Application 96/00234, published Jan. 4, 1996, clinically adequate labeling of the human chromosomes was not obtained. International Application WO 96/31626, published Oct. 10, 1996, is hereby incorporated by reference as to the teaching of a glycerol-based hybridization solution and the use of a glycerol-based hybridization solution with biological DNA probes. International Application WO 96/00234, published Jan. 4, 1996, is hereby incorporated by reference as teaching synthetic oligonucleotide clone probes specific for human chromosomes X, Y, 13, 18 and 21 useful with the present invention. Biologic probes are taught by Gray & Pinkel, U.S. Pat. No. 5,447,841, hereby incorporated by reference.

As taught in the parent application, it was found necessary to modify the glycerol-based hybridization methodology taught in International Application WO 96/31626, to adapt it for use with synthetic oligonucleotide DNA probes. Specifically, it was found that reducing the hybridization temperature from 55° C. to between 37 and 47° C., changing the sodium ion concentration in the wash, and reducing the wash temperature from 65° to a temperature which was substantially the same as the hybridization temperature, i.e., between 37 and 47° C., yielded acceptable specific binding and retention of the fluorophore labeled synthetic oligonucleotide probe to human chromosomes X, Y, 13, 18 and 21 in lymphocytes, amniocytes, and metaphase chromosomes. In accordance with the best mode of the present invention, however, it was found that while the bound fluorescence signal was acceptable, the signal was not conserved sufficiently to achieve an acceptable duration of the fluorescence signal. It was further discovered that the addition of dithiothreitol to the hybridization buffer achieved a prolonged duration of the bound fluorescence signal and permitted the labeled samples to be archival stored and analyzed at a later time.

For each of the inventive FISH protocols, the chromosome-labeling process was completed within 90 minutes. The inventive processes are based upon a unique formamide-free hybridization chemistry that enhances the probe-to-target annealing reaction without compromising hybridization efficiency, specificity, or cellular and nuclear morphology. The inventive FISH processes use synthetic oligomeric probes with sequences derived from the alpha satellite regions of human chromosomes X, Y, 13, 18, and 21. Hybridization specificity and efficiency, and chromosomal target were retained through the repetitive hybridization processing on the same sample. The inventive formamide-free hybridization chemistry is readily adapted for use with different cell types. The simple and rapid methods developed with this chemistry work with either lymphocytes, uncultured amniocytes or metaphase chromosomes, and with cells fixed by different methods.

The inventive ReFISH process introduces the possibility of FISH analysis for multiple chromosome targets with a sample that is small or otherwise limited by generating simple patterns for each analysis, without the need to have complex mixtures of different probes. This avoids the interpretation of more complex signal patterns when multiple-target probe mixtures are used in a single reaction. Another advantage of ReFISH is that archived samples can be reexamined by FISH at a later date, i.e., several weeks or even months later, either for re-confirmation or with another probe set that was not requested or available at the time of initial testing.

SUMMARY OF THE INVENTION

A primary objective of the present invention is to provide carbinol-based hybridization buffers which permit hybridization either with or without the presence of dextran sulfate, to label DNA and RNA using carbinol containing hybridization buffers. The inventive processes herein described are based upon a unique hybridization chemistry that is not dependant upon the presence of formamide. This novel methodology preserves cellular and nuclear morphology during the denaturation and hybridization steps, while yielding a target-specific signal of high intensity in less than one hour for most cells. To demonstrate the efficiency of this carbinol-based hybridization method, we present a simple FISH protocol using lymphocytes and cells isolated from umbilical cord blood. The inventive protocol was developed with the objective of simplifying the whole FISH labeling process, using a minimal number of steps for sample preparation, fixation, denaturation, hybridization, and post-hybridization washing.

It is a still further objective of the present invention to conduct ISH in the presence of a carbinol containing hybridization buffer and in the presence of biologic or synthetic probes. It is desirable that the synthetic oligonucleotide probes have from less than about 75 bases, preferably between 15 and 75, and most preferably between 25 and 35 bases. The process denatures the cellular DNA by heating the sample to about 90–100° C. for about 1.5–5 min, hybridizing the probe and the sample between about 42 to 85° C. for between about 5 to 60 min, preferably between 15 and 60 min, for lymphocyte samples, and washing the post-hybridization sample to remove non-specifically bound probe and retain specifically bound probe.

It is another objective of the present invention to provide a FISH methodology for carbinol-based hybridization of synthetic oligonucleotide DNA probes specific for the centromeric regions of target chromosomes.

It is a further objective of the present invention to provide an improved FISH methodology for hybridizing DNA probes utilizing a carbinol containing hybridization buffer wherein the optimum temperature of hybridization conditions are calculated according to the formula:

$$T_{hyb}=[(16.6 \log(Na^+)+0.41(\% \ G+\% \ C)+81.5)-500/L]-X$$

where, $Na^+$ is equal to the concentration of sodium cations, % G is equal to the molar percent of guanine bases in the probe or target DNA sequence and % C is equal to the molar percent of cytosine bases in the probe, or target DNA sequence, where X is an integer between 18 and 30.

These and other objects, features and advantages of the present invention are more readily understood by those of ordinary skill in the art from the following more detailed description of the preferred embodiments of the present invention taken with reference to the accompanying figures.

DETAILED DESCRIPTION OF THE PREFERRED EMBODIMENTS

Figure 1:
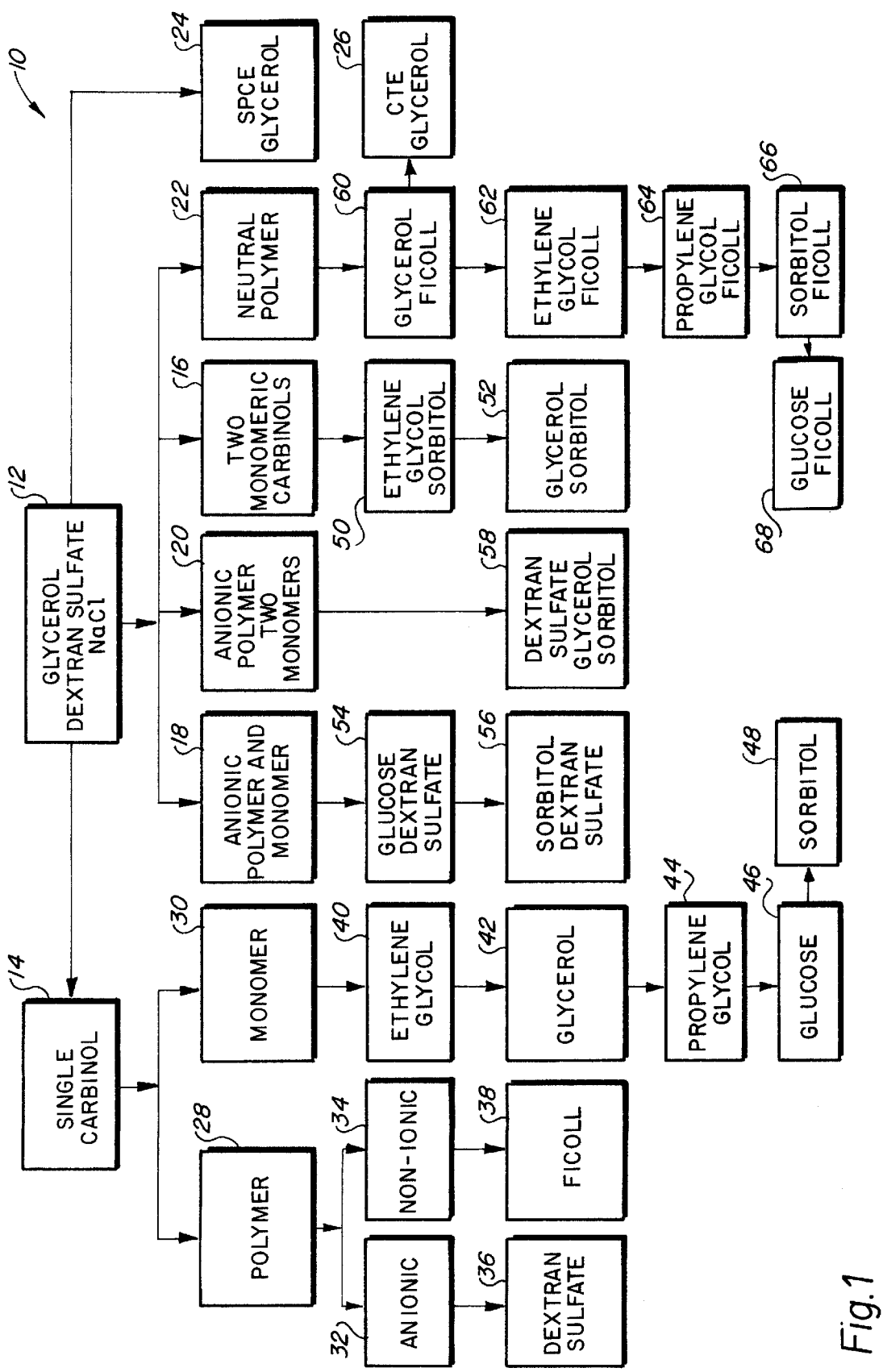
FIG. 1 is a decisional chart illustrating the experimental procedures conducted to determine the efficacy of carbinol-based hybridization buffers.

International Application WO 96/31626 teaches that when used with biologic probes, a hybridization buffer consisting of glycerol and dextran sulfate, will successfully bind fluorescent signal in using fluorescence in situ hybridization techniques. However, it was found that when that same protocol was utilized with clone probes, it was unsuccessful. Successful FISH was then carried out with in the presence of modified hybridization and wash conditions. Replication of International Application WO 96/31626: Solution G, Denaturation and Hybridization Conditions with Aprogenex Synthetic Oligonucleotide Probes 16 µg/ml of Aprogenex XY probe in Solution G from International Application WO 96/31626 (20% glycerol (v/v), 10% dextran sulfate (w/v) and 0.9% NaCl (w/v)) was added to a glass slide and covered with a circular coverslip. The sample slide was then heated at 100° C. for 1.5 min to denature the chromosomal DNA, then hybridized at 42° C. for 30 min followed by washing in accordance with the Aprogenex APROPROBE PLUS wash protocol incorporated by reference. The resulting sample was then counterstained with DAPI and analyzed for bound fluorescence signal. It was determined that the hybridization efficiency was approximately 97.4% with moderate bound signal (scored as 2–3 on a scale of 1 to 5).

To then determine the effect of the wash type on hybridization, the conductivity of the Aprogenex APROPROBE PLUS washes was measured and wash solutions based upon the wash solution system taught in International Application WO 96/31626, i.e., NaCl and NP-40, was devised. It was found that the conductivity of the Aprogenex Wash A was measured at 3500 µS and the conductivity of Aprogenex Wash B was measured at 2600 µS. A NaCl and NP-40 solution having conductivity of about 3500 µS was made by admixing 0.35 M NaCl with 0.15% NP-40 (hereinafter "Saline Wash A) and a NaCl and NP-40 solution having conductivity of about 4800 µS was made by admixing 0.035 M NaCl with 0.15% NP-40 (hereinafter "Saline Wash B"). The hybridization reaction was carried out as described above in this section and the hybridized sample was washed in Saline Wash A for 3 min at 42° C., followed by four washes in Saline Wash B, with each wash being for 30 sec at 42° C. It was determined that the glycerol-based hybridization solution was not dependent on the Aprogenex Wash A and Wash B solutions, and moderate bound signal was conserved using the Saline Wash A and Saline Wash B protocol.

Replication of international Application WO 96/31626: Solution G Plus DTT, Denaturation and Hybridization Conditions with Aprogenex Synthetic Oligonucleotide Probes In the foregoing example, while there was moderate bound signal obtained using the inventive denaturation and hybridization conditions with the synthetic oligonucleotide probes and the glycerol-based hybridization medium, it was found that the duration of the signal was transient. Accordingly, a methodology was devised to stabilize the bound signal when using a glycerol-based hybridization solution in which a reducing agent, such as dithiothreitol (DTT), dithioerythritol, mercaptoethanol, or tris (2-carboxyethyl)phosphine is added to the glycerol-based hybridization solution.

16 µg/ml of Aprogenex XY probe in Solution G from International Application WO 96/31626 (20% glycerol (v/v), 10% dextran sulfate (w/v) and 0.9% NaCl (w/v)) and 100 mM DTT was added to a glass slide and covered with a circular coverslip. The sample slide was then heated at 100° C. for 1.5 min to denature the chromosomal DNA, then hybridized at 42° C. for 30 min followed by washing in Saline Wash A for 3 min at 42° C., followed by four washes in Saline Wash B, with each wash being for 30 sec at 42° C. The resulting sample was then counter-stained with DAPI and analyzed for bound fluorescence signal and duration of signal. It was determined that the signal was bound and, when compared to a control sample, without DTT, only the sample processed with the DTT had a signal which did not quickly fade. To determine whether the presence of DTT drove hybridization, subsequent experiments were conducted using a hybridization buffer without glycerol, but with only dextran sulfate, saline and DTT, and it was found that the absence of the glycerol component from the hybridization buffer did not drive hybridization of the synthetic oligonucleotide probes. Further experiments tested whether DTT, with only glycerol and saline, and without dextran sulfate drove hybridization. It was found that the absence of dextran sulfate from the hybridization medium, in the presence of DTT, did drive hybridization of the synthetic oligonucleotide clone probes.

Alternative Hybridization Buffers

In order to test alternative hybridization reagents, the present invention tested various monomeric and polymeric carbinol compounds to determine their efficacy as a hybridization buffer for both in situ and blot hybridizations. It has been found that carbinols having the general formula I exhibit utility as hybridization buffers in accordance with the present invention.

Where n is an integer between 2 and 5, x is an integer between 2 and 6 and $R_1$ is a selected from the group consisting of H, $CH_3$ and CHO and y is an integer greater than or equal to 1. In accordance with the present invention it has been found particularly desirable to select a monomeric carbinol from the group consisting of ethylene glycol, propylene glycol, glycerol, sorbitol, and glucose. Additionally, the polymeric carbinols may preferably be selected from the group consisting of Ficoll, a neutral, highly branched polysucrose, polyethylene glycol, and dextran sulfate. The hybridization buffer may be selected to have a single monomeric carbinol, a single polymeric carbinol, a combination of monomeric carbinols, a combination of a monomeric carbinol with a polymeric carbinol and a combination of polymeric carbinols.

FIG. 1 is a decisional flow chart illustrating the in situ hybridization testing methodology 10 for the following examples. The starting point for the testing methodology 10 is to employ G-buffer as described in International Application WO 96/31626, under the hybridization and wash conditions as described above on samples of umbilical cord blood. For each of the substitution experiments, denaturation was conducted at a temperature between 90° C. and 100° C. for 1.5 minutes, the hybridization temperature was maintained between 42 and 55° C., the NaCl concentration was maintained at 154 mM, when present, using either the Aprogenex probes or the Vysis probes, more fully described above. Substitutions of carbinols having the general formula I, above, for glycerol in the G-buffer, are made using either a single monomeric carbinol 14, two monomeric carbinols 16, an anionic polymeric carbinol and a single monomeric carbinol 18, an anionic polymeric carbinol and two monomeric carbinols 20, a neutral polymeric carbinol 22, glycerol, NaCl and CTE buffer (5 mM Citric Acid, 12.5 mM Tris, and 5 mM Tris) 26 or glycerol and SPCE buffer (142.7 mM NaCl, 11.6 mM $NaH_2PO_4$, 23.3 mM $Na_2CO_3$ and 5.0 mM EDTA) 24. Since SPCE includes sodium chloride, the glycerol/SPCE hybridization solution does not include additional sodium chloride.

To test individual carbinols 14, exemplary polymeric carbinols 28 and exemplary monomeric carbinols 30 were selected. The monomeric carbinols 30 selected included ethylene glycol 40, glycerol 42, propylene glycol 44, glucose 46 and sorbitol 48. The polymeric carbinols 28 selected were divided into examples of an anionic polymeric carbinol 32, namely dextran sulfate 36, and a neutral polymeric carbinol 34, namely Ficoll (polysucrose) 38. Where combinations of two carbinols were tested 16, ethylene glycol and sorbitol combined at step 50 and glycerol and sorbitol were combined at step 52.

To test combinations of an anionic polymer with a monomeric carbinol 18, combinations of dextran sulfate with glucose 54 and with sorbitol 56 were tested. To test a combination of an anionic polymer with two monomeric carbinols, dextran sulfate was combined with glycerol and sorbitol. 58.

A neutral carbinol-based polymer, Ficoll-400 (polysucrose), was tested alone 22, and in combination with single monomeric carbinols glycerol 60, ethylene glycol 62, propylene glycol 64, sorbitol 66 and glucose 68.

Figure 2:
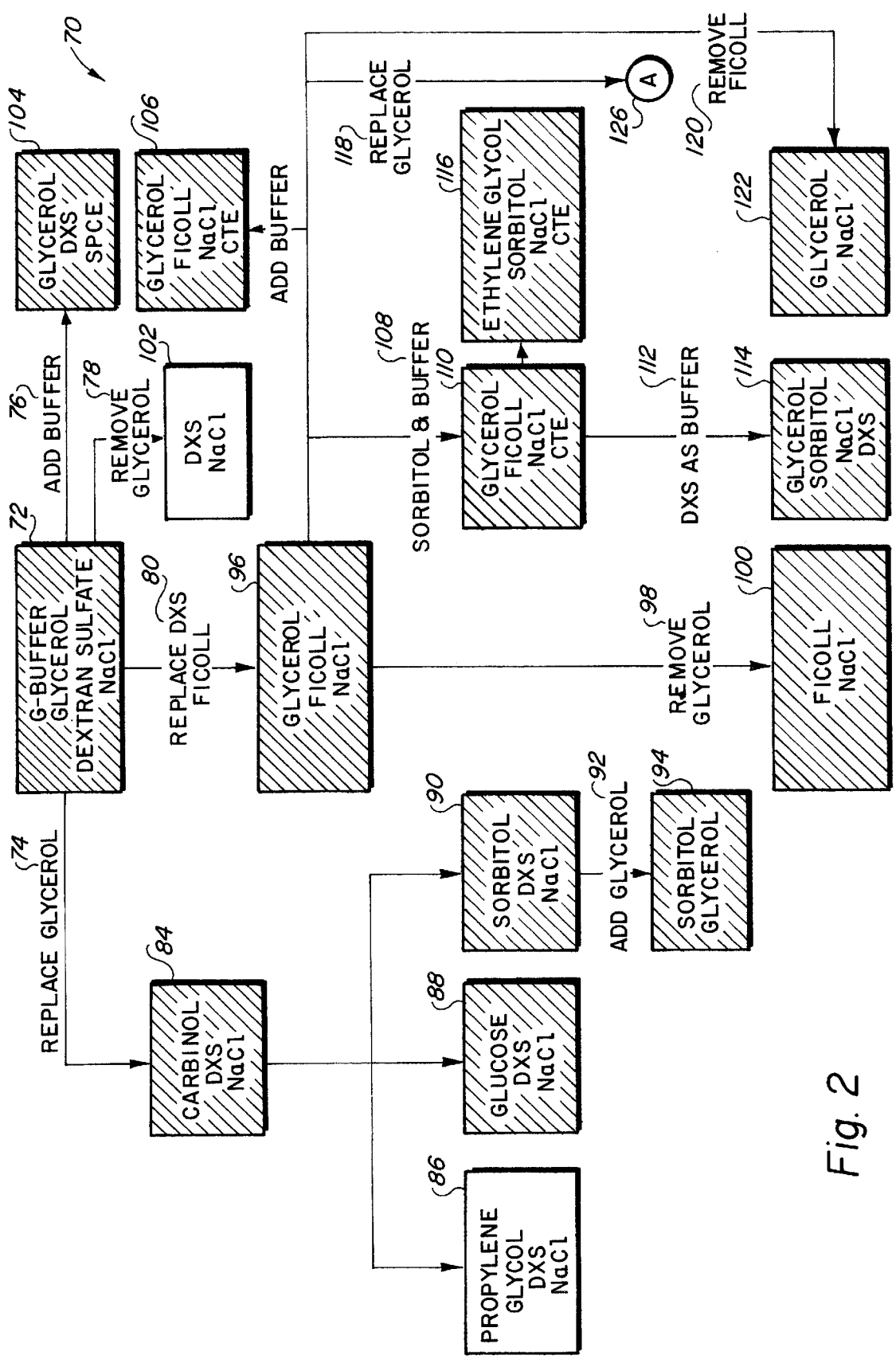
FIG. 2 is an experimental flow chart illustrating the experimental procedures conducted to verify the efficacy of carbinol-based hybridization buffers for fluorescence in situ hybridization.
Figure 3:
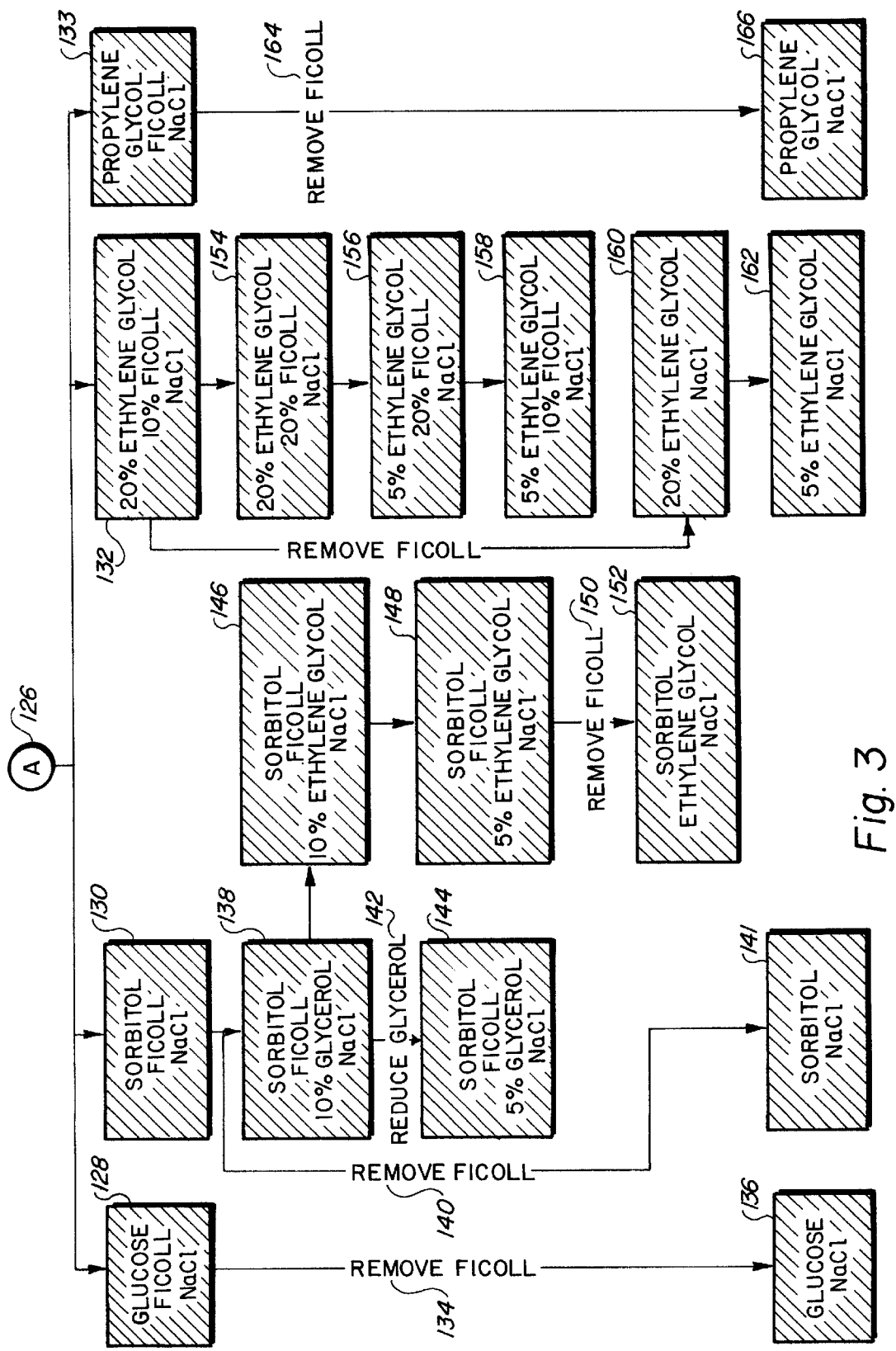
FIG. 3 is an experimental flow chart continuing from FIG. 2.

Turning now to FIGS. 2 and 3, the foregoing series of experiments conducted are described in greater detail. For purposes of clarity, the boxes representing successful experiments, i.e., those which resulted in detectable fluorescent signal binding, have been shaded, while the boxes representing unsuccessful experiments are unshaded. In the following Examples, the corresponding box reference numeral in FIGS. 2 and 3 is identified in parentheses.

EXAMPLE 1 (72)

16 µg/ml of Aprogenex XY probe in G-buffer (20% glycerol (v/v), 10% dextran sulfate (w/v) and 0.9% NaCl (w/v)) was added to a glass slide and covered with a circular coverslip. The sample slide was then heated at 100° C. for 1.5 min to denature the chromosomal DNA, then hybridized at 42° C. for 30 min followed by washing in accordance with the post-hybridization wash protocol described hereinafter. The resulting sample was then counter-stained with DAPI and analyzed for bound fluorescence signal. It was determined that the hybridization efficiency was approximately 97.4% with moderate bound signal (scored as 2–3 on a scale of 1 to 4).

EXAMPLE 2 (86)

The same steps were conducted as in Example 1, except that propylene glycol was substituted at the same concentration (20%) for the glycerol. No detectable fluorescence labeling of the chromosomal DNA was obtained.

EXAMPLE 3 (88)

The same steps were conducted as in Example 1, except that glucose was substituted at the same concentration (20%) for the glycerol. There was a detectable fluorescence labeling of the chromosomal DNA.

EXAMPLE 4 (90)

The same steps were conducted in Example 1, except that sorbitol was substituted at the same concentration (20%) for the glycerol. There was a detectable fluorescence labeling of the chromosomal DNA.

EXAMPLE 5 (94)

The same steps were conducted as in Example 4, except that glycerol was added to the hybridization buffer at a concentration of 5% (v/v). Again, there was a detectable fluorescence labeling of the chromosomal DNA.

EXAMPLE 6 (104)

The same steps were conducted as in Example 1, except that SPCE buffer (142.7 mM NaCl, 11.6 mM $NaH_2PO_4$, 23.3 mM $Na_2CO_3$ and 5.0 mM EDTA) was substituted for the NaCl. This substitution yielded a detectable fluorescence label of the chromosomal DNA.

EXAMPLE 7 (102)

The same steps were followed as in Example 1, except that the glycerol was removed, yielding a hybridization buffer of dextran sulfate and NaCl. The results indicated that the absence of glycerol interfered with fluorescence labeling and there was no detectable labeling of the chromosomal DNA.

EXAMPLE 8 (96)

The same steps were followed as in Example 1, except that Ficoll-400 was substituted at the same concentration (10%) for the dextran sulfate. It was found that this hybridization buffer yielded a detectable fluorophore labeled chromosomal DNA. This example was repeated, using each of the Vysis biologic probe and the Aprogenex synthetic oligonucleotide probe, with both cases yielding a detectable fluorescence specifically bound signal.

EXAMPLE 9 (106)

The same steps were conducted as in Example 1, except that CTE buffer (5 mM Citric Acid, 12.5 mM Tris, and 5 mM Tris) was added and Ficoll-400 was substituted for the dextran sulfate at an equivalent concentration (10%). The combination of CTE buffer with the substitution of Ficoll for the dextran sulfate yielded a detectable fluorescence labeling of the chromosomal DNA.

EXAMPLE 10 (100)

The same steps were followed as in Example 1, except that the glycerol component of the hybridization buffer was removed. It was found that in the absence of glycerol, the presence of the neutral polymeric carbinol Ficoll was sufficient to obtain a detectable fluorescence label of the chromosomal DNA.

EXAMPLE 11 (110)

The same steps were followed as in Example 8, except that the Ficoll was eliminated and sorbitol (20%) was added in place of the Ficoll, and in the presence of CTE buffer (1×). This hybridization buffer composition yielded detectable fluorescent labeling of the chromosomal DNA.

EXAMPLE 12 (114)

The same conditions as in Example 11 were employed, except that dextran sulfate (1%) was substituted for the CTE buffer. Acceptable fluorescent labeling of the chromosomal DNA was achieved.

EXAMPLE 13 (116)

The same conditions as in Example 11 were employed, except that ethylene glycol was substituted at the same concentration (20%) for the glycerol. Again, acceptable fluorescent labeling of the chromosomal DNA was achieved.

EXAMPLE 14 (122)

The conditions of Example 8 were repeated, except that the Ficoll component was eliminated, yielding a hybridization buffer composed of glycerol (20%) and NaCl (154 mM). Glycerol, in the absence of the Ficoll was found enhance specific binding of the flourescent probe to the chromosomal DNA, yielding detectable labeled target.

EXAMPLE 15 (128)

The conditions of Example 8 were employed, except that glucose was substituted for the glycerol. It was found that acceptable fluorescent labeling of the chromosomal DNA was achieved.

EXAMPLE 16 (136)

The conditions of Example 15 were employed, except that the Ficoll was removed from the hybridization buffer. It was found that acceptable fluorescent labeling of the chromosomal DNA was achieved.

EXAMPLE 17 (130)

The conditions of Example 8 were employed, except that sorbitol was substituted at the same concentration (20%) for the glycerol. It was found that acceptable fluorescent labeling of the chromosomal DNA was achieved.

EXAMPLE 18 (138)

The conditions of Example 17 were employed, except that 10% glycerol was added to the hybridization buffer. Acceptable fluorescent labeling of the chromosomal DNA was achieved.

EXAMPLE 19 (144)

The conditions of Example 18 were followed, except that the concentration of glycerol was reduced to 5%. Again, acceptable fluorescent labeling of the chromosomal DNA was noted.

EXAMPLE 20 (141)

The conditions of Example 17 were followed, except that the Ficoll component was removed from the hybridization buffer. It was found that sorbitol, in the absence of Ficoll, also enhanced specific binding of the fluorescent probe and that detectable fluorescent signal was achieved.

EXAMPLE 21 (146)

The conditions of Example 18 were followed, except that ethylene glycol was substituted at an equivalent concentration (10%) for the glycerol. It was found that the substitution of ethylene glycol for the glycerol also enhanced specific binding of the fluorescent probe and that detectable fluorescent signal was achieved.

EXAMPLE 22 (148)

The conditions of Example 21 were followed, except that the concentration of ethylene glycol was reduced to 5%. Again, it was found that substitution of a lower concentration of ethylene glycol for glycerol was effective in achieving detectable bound signal.

EXAMPLE 23 (152)

The conditions of Example 22 were followed, except that the Ficoll was removed from the hybridization buffer. The results indicated that the lower concentration of ethylene glycol, in the absence of Ficoll, also enhanced detectable bound signal and acceptable fluorescent signal was achieved.

EXAMPLE 24 (132)

The conditions of Example 8 were employed, except that ethylene glycol was substituted at an equivalent concentration (20%) for the glycerol. Acceptable specifically bound fluorescent signal was detected.

EXAMPLE 25 (154)

The experimental conditions of Example 24 were followed, except that the concentration of Ficoll was increased to 20%. The increased concentration of Ficoll was found to enhance specific binding of the fluorophore-labeled probe and detectable signal was achieved.

EXAMPLE 26 (156)

The experimental conditions of Example 25 were employed, except that the concentration of ethylene glycol was reduced to 5%, the reduced concentration of glycol still enhanced specific binding of the labeled probe and delectability of the fluorescent signal.

EXAMPLE 27 (158)

The experimental conditions of Example 26 were followed, with a reduction in the Ficoll concentration to 10%. Again, there was acceptable detectable bound fluorescent signal.

EXAMPLE 28 (160)

The conditions of Example 24 were followed, except that the Ficoll was removed from the hybridization buffer. Acceptable specifically bound detectable signal was noted.

EXAMPLE 29 (162)

The conditions of Example 28 were followed, except that the concentration of ethylene glycol was reduced from 20% to 5%, with enhanced delectability of specifically bound fluorescent signal to chromosomal DNA.

EXAMPLE 30 (133)

Example 8 was followed, except that propylene glycol was substituted at an equivalent concentration (20%) for the glycerol, with the result being that acceptable bound signal was detected.

EXAMPLE 31 (166)

Example 30 was followed, except that the Ficoll component of the hybridization buffer was eliminated. Acceptable bound signal was detectable.

From Table 1, below, it will be seen that the hybridization efficiencies for both nucleated erythrocytes (NRBC) and lymphocytes (WBC) for selected examples above was quite good, thereby, assuring a high confidence level for specific binding under the hybridization conditions noted in each example.

TABLE 1

Hybridization Efficiencies

| Example No. | HE NRBC (%) | HE WBC (%) | Temp ° C. (hyb/wash) | Hyb Time (min) |
|---|---|---|---|---|
| 16 | 99 | 99 | 42/42 | 15 |
| 18 | 99 | 98 | 42/42 | 30 |
| 22 | 98 | 100 | 42/42 | 30 |
| 25 | 100 | 96 | 42/42 | 30 |
| 31 | 87 | 98 | 42/42 | 15 |
| 7 | 99 | 99 | 50/50 | 30 |
| 9 | 93 | 98 | 47/42 | 30 |

EXAMPLE 33

The hybridization buffer composition from Example 9 (20% Glycerol, Ficoll-400 10%, NaCl 154 mM) was used, and the hybridization temperature was varied between 42 and 85° C. and the wash temperatures were varied between 42 and 50° C. Table 2, below, represents the results of this Example, which illustrates that the a broad range of hybridization and wash temperatures are useful for hybridization and washing, with acceptable bound signal being achieved at hybridization and wash temperatures above 42° C. and less or equal to 85° C. hybridization temperature and less than or equal to 55° C. for the wash temperature.

TABLE 2

Bound Signal as a Function of Hybridization and Wash Temperatures Using Glycerol-Ficoll-NaCl Hybridization Buffer (Ref. 96)

| Hybridization Temp. (° C.) | Wash Temp. (° C.) | Result (X of 4) |
|---|---|---|
| 42 | 42 | +++ |
| 45 | 45 | +++ |
| 47 | 47 | +++ |
| 49 | 49 | ++++ |
| 55 | 55 | +++ |
| 50 | 50 | +++ |
| 60 | 47 | +++ |
| 65 | 47 | +++ |
| 70 | 50 | +++ |
| 85 | 50 | +++ |
| 47 | 47 | +++ |

EXAMPLE 34

The hybridization buffer composition from Example 8 (20% Glycerol, Ficoll-400 10%, NaCl 154 mM) was used to test whether probe type affected the specificity of signal binding to chromosomal DNA. Biologic probes (Vysis, Inc.) and synthetic probes (Aprogenex, Inc.) specific for X, Y and γRNA were tested using constant hybridization and wash conditions. As reflected in Table 3, below, probe type was found to have no qualitative effect on the specificity of the bound signal or the detected fluorescent signal.

TABLE 3

Bound Signal as a Function of Probe Type

| Probe Type | Hybridization Temp. (° C.) | Wash Temp. (° C.) | Result (X of 4) |
|---|---|---|---|
| Vysis | 60 | 47 | +++ |
| Aprogenex | 60 | 47 | +++ |

In Situ Hybridization Protocols

The following summarizes preferred protocols for in situ hybridization of lymphocytes and umbilical cord blood as used in the foregoing examples and which have been found useful with the single monomer, dual monomer, and polymeric carbinol hybridization buffer compositions of the present invention.

Protocol 1: Lymphocyte In-Situ Hybridization

The cell preparation protocol and FISH process used with lymphocytes and umbilical cord blood are described below.
Sample Preparation and Fixation
1) Centrifuge cells through PBS (Sigma P-4417) spinning for 5 min at approximately 300×gravity using a cell centrifuge.
2) Air dry for at least 10 min. no longer than 60 min.
3) Fix in fresh (3:1 v/v) Ethanol: Methanol for 10 min,
4) Air-dry slide.
5) Incubate on bench overnight.
6) Store frozen with desiccant.
Post-fixation
7) Soak in fresh (3:1) Ethanol:Methanol for 15 seconds at room temperature.
8) Air-dry slide for at least 10 min.
Hybridization
9) Apply 10 µl of probe/buffer cocktail to a sample area of 18 to 22 mm in diameter.
10) Apply a round coverslip to the sample area to distribute the cocktail across the sample.
11) Heat slide to 100° C. for 90 to 110 sec.
12) Incubate slide at 42° C. for 30 min.
Post-Hybridization Wash (all Washing Steps are at 42° C.)
13) Soak slide (with coverslip) for 1 min in 1/10 dilution of 20×SSC (1×SSC equals 0.15 M NaCl, 0.015M sodium citrate).
14) Remove coverslip
15) Soak slide for 3 min in 1/10 dilution of 20×SSC
16) Transfer the slide to the first of four Coplin jars all containing 1/100 dilution of 20×SSC (0.0339 M Na+) and soak for 30 seconds
17) Repeat the above step subsequently with the second through fourth Coplin jars with 1/100 dilution of 20×SSC
18) Air-dry slide
19) Apply mounting medium (VECTASHIELD, Vector Laboratories, Inc., Burlingame, Calif. (99% glycerol), DAPI (20–300 ng/mL), NaCl 0.8 M)
20) Apply 22 mm coverslip, view by epifluorescent microscopy The resulting slides may be stored in a light-tight container, either refrigerated or frozen, and the labeling has been found stable for at least 3 months.

Blot Hybridization Methadology
Probe Synthesis Protocol 3 ug of plasmid DNA (pBR322, Boehringer Mannheim) were digested with Bgl 1 in a 10 ul volume using 1 unit of restriction enzyme for 2 hours at 37 degrees C. Digesting was stopped by heating the reaction in a boiling water bath for 10 min. 5 uL of High Prim reaction mix and water were added to the digested plasmid solution to a final volume of 20 uL. The labeling reaction was incubated for approximately 23 hours at 37° C. The labeling reaction was stopped by heating in a boiling water bath for 10 min. The labeling solution was diluted with 55 uL of HPLC water to a final pBR322 DNA concentration of 40 ug/mL.
Target DNA Preparation 2 ug of plasmid DNA (pBR322, Boehringer Mannheim) were digested with Bgl 1 in a 20 ul volume using 1 unit of restriction enzyme for 2 hours at 37 degrees C. Digesting was stopped by heating the reaction in a boiling water bath for 10 min.
Dot Blot Hybridization Dot blots were made using a Pierce EASY-TITER ELIFA System manifold. The blots were of neutral 0.22 micron nylon membranes (MAGNAGRAPH, Micron Separations, Inc.). Just prior to placing in the manifold, the membrane was wetted in distilled water. The DNA target (Bgl 1-digested pBR322) was applied to the membrane as a stock solution of 1.5M NaCl/0.5M NaOH with 20 ug/mL of sheared herring sperm DNA. The pBR322 DNA was dissolved in this solution at the highest concentration of $1\times10^{-7}$ g/mL with the lowest at $1\times10^{-12}$ g/mL. Each blot had 8 rows, with 3 dots per row. The first row had 100 uL of highest concentration of target DNA ($1\times10^{-8}$ g per dot), the second row was a 0.1×dilution, the third dot was a 0.01× dilution, with each successive row having a log-fold less DNA with the sixth row having $1\times10^{-15}$ g pBR322 per dot. Row 7 was a control containing herring sperm DNA and row 8 was a control with 0.1 ml of 1.5 M NaCl/0.5 M NaOH. After applying the DNA to each dot, the well was rinsed with 0.2 mL of deionized water and the suction applied for an additional 5 minutes before removing the blot from the manifold. The blot was air dried at 37° C. for at least 12 hours.

The blots were prehybridized in their respective hybridization buffers (0.05 mL/cm$^2$) for 1 hour at 37°. The blots were removed from the prehybridization solution and placed face down in 2 mL of probe hybridization cocktail (hybridization buffer with 40 ng/mL of heat denatured dig-labeled pBR322 probe) at 60° C. The blots were then placed on a slide warmer at 60° C. for 1–3 hours.

Hybridization Wash A (2×SPCE [1×SPCE=142.7 mM NaCl, 20 mM NaH$_2$PO$_4$, 11.65 mM Na$_2$CO$_3$, 5 mM Na$_2$EDTA, pH7.3]/0.1% SDS) was employed with each sample for 15 min at room temperature in 60 mL/blot, Wash B (0.2×SPCE/0.1% SDS) for 5 min at room temperature in 60 mL/blot, followed by Wash C (0.2×SPCE/0.1% SDS) for 15 minutes, with the wash temperature at 60° C. at wash introduction, and incubation at room temperature. After washing, the blot is transferred to TBS (20 mM Tris pH 7.5, 150 mM NaCl) and incubated for 5 min at room temperature. The blot was first incubated in blocking buffer 9(9:1) TBS:10×Blocking Solution (Boehringer Mannheim Kit 1745832) for 30 min at 37° C. Antibody labeling was performed at 37° C. for 30 min, using 2–3 mL of antibody (anti-DIG-alkaline phosphatase conjugate) solution, a 1:5000 dilution of antibody in blocking buffer. The blot was washed twice at room temperature, 15 minutes each in TBS:0.2% Tween 20, followed by 10 min incubation in detection buffer (100 mM Tris-HCl, pH9.0, 100 mM NaCl, 5 mM MgCl). The blot was then developed for 14–16 hours using BCIP/NBT solution (20 uL/mL of BCIP/NBT stock (Boehringer Mannheim) in detection buffer), 2 mL to 3 mL per blot. Color development was stopped by soaking the blot in deionized water.

Figure 4:
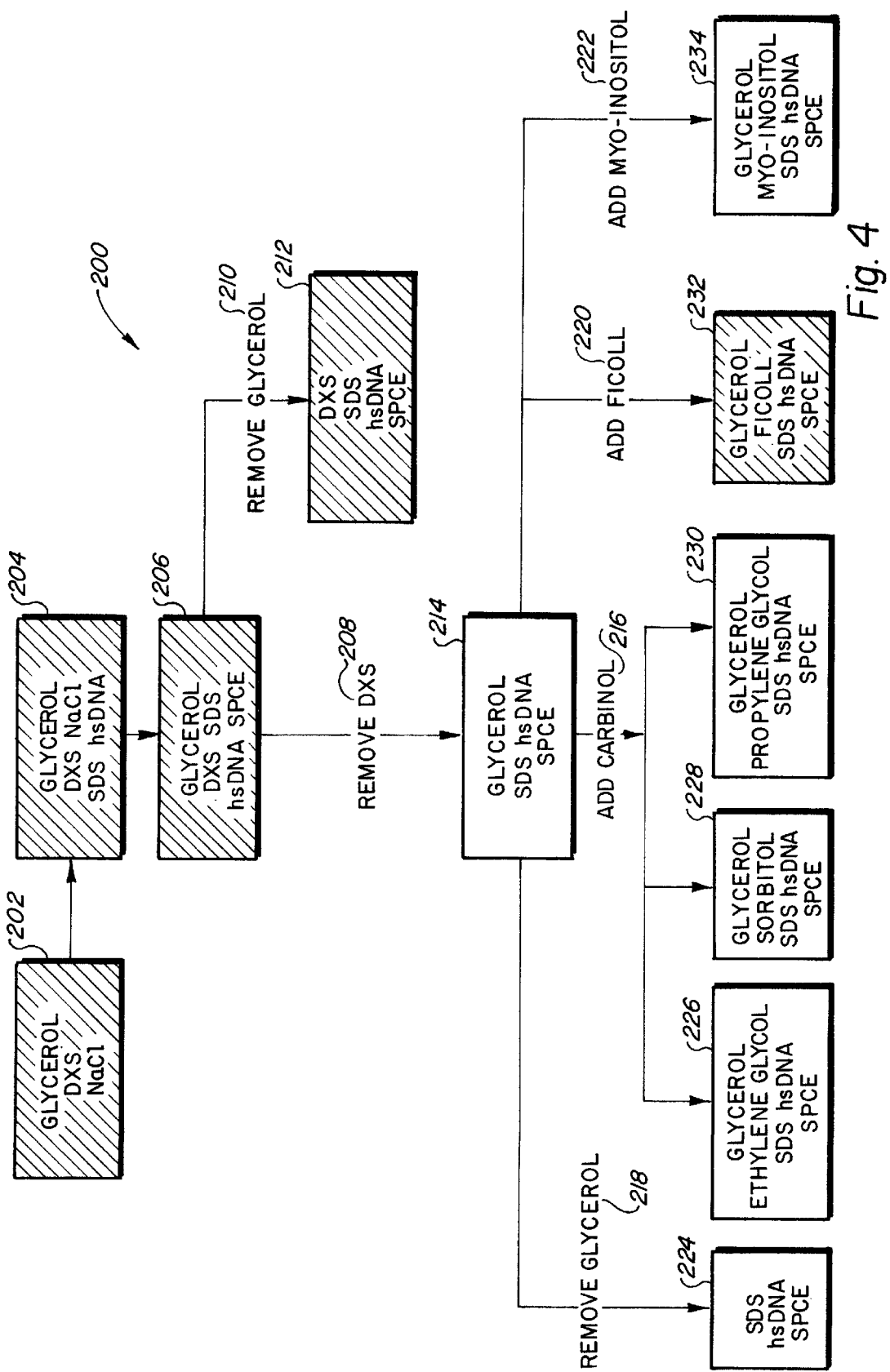
FIG. 4 is an experimental flow chart illustrating the experimental procedures conducted to verify the efficacy of carbinol-based hybridization buffers for blot hybridization.

The hybridization buffers tested each contained identical Na⁺ ion concentration of 0.154 M, 0.5% SDS and 200 ug/mL of sheared, denatured herring sperm DNA. The hybridization buffers differed only in the carbinol and the presence or absence of dextran sulfate or Ficoll. As more fully reflected in FIG. 4, which reflects the decisional methodology employed to test the inventive hybridization buffers in blot hybridization, the following hybridization buffers were tested: glycerol/dextran sulfate, glycerol/dextran sulfate/SPCE, dextran sulfate/SPCE, glycerol/ethylene glycol/SPCE, glycerol/sorbitol/SPCE, glycerol propylene glycol/SPCE, glycerol/Ficoll/SPCE, and glycerol/myo-inositol/SPCE. The control buffer was SPCE alone. Table 4, below, summarizes the results of efficacy of carbinol-based hybridization buffers in blot hybridizations where a minus sign (−) designates the absence of a constituent compound or an enhanced signal over the control signal, and a plus sign (+) designates the presence of a constituent compound or an enhanced signal over the control.

TABLE 4

| Carbinol | DXS | Ficoll | SPCE | Enhanced Signal |
|---|---|---|---|---|
| [Control] | − | − | + | − |
| glycerol | + | − | − | + |
| glycerol | + | − | + | − |
| — | + | − | + | + |
| glycerol | − | − | + | − |
| glycerol/ethylene glycol | − | − | − | − |
| glycerol/sorbitol | − | − | + | − |
| glycerol/propylene glycol | − | − | + | + |
| glycerol | − | + | + | + |
| glycerol/myo-inositol | − | − | + | − |

It will be appreciated, from the foregoing, that the efficacy of a carbinol-based hybridization buffer, or an anionic or a neutral polymeric carbinol-based buffer, in either in situ hybridization procedures or in dot blot hybridizations cannot be considered predictive of its efficacy in other hybridization methodologies.

While the present invention has been described with reference to its preferred embodiments and the foregoing examples, those of ordinary skill in the art will understand and appreciate that the scope of the present invention is not limited by the foregoing examples or reaction conditions, but only by the claims appended hereto.

What is claimed is:

1. A hybridization method for hybridizing labeled nucleic acid probes to nucleic acid sequences to form labeled hybridized complexes, comprising the steps of:
    a) denaturing nucleic acid sequences within an isolated population of biological matter;
    b) hybridizing labeled, nucleic acid probes having less than or equal to 75 bases with specific portions of the denatured nucleic acid sequences in the presence of a carbinol-based formamide-free hybridization buffer to form labeled hybridized complexes, the hybridization being carried out at a temperature between about 42° C. and about 85° C.; and
    c) washing the labeled hybridized complexes, the washing being carried out at a temperature between about 47° C. and 55° C.

2. The hybridization method according to claim 1, wherein step b further comprises the step selecting a carbinol compound in the carbinol-based hybridization medium, the carbinol compound having the general formula:

wherein n is an integer between 2 and 5, x is an integer between 2 and 6 and $R_1$ is a selected from the group consisting of H, $CH_3$ and CHO and y is an integer greater than or equal to 1.

3. The hybridization method according to claim 1, wherein step b further comprises the step of selecting a hybridization buffer for hybridizing nucleic acid probes to nucleic acid sequences, comprising a carbinol compound having the general formula:

wherein n is an integer between 2 and 5, x is a integer between 2 and 6 and $R_1$ is selected from the group consisting of $H_1$, $CH_3$ and CHO and y is an integer greater than or equal to 1.

4. The hybridization method according to claim 1, wherein the hybridization temperature and the wash temperature are selected to be substantially the same as one another.

* * * * *